US00PP13750P29

(12) United States Plant Patent
Lemon

(10) Patent No.: US PP13,750 P2
(45) Date of Patent: Apr. 29, 2003

(54) GERANIUM PLANT NAMED 'ELEGANCE PINK CHIFFON'

(75) Inventor: David Lemon, Santa Barbara County, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 10/245,038

(22) Filed: Sep. 17, 2002

(51) Int. Cl.[7] ..... A01H 5/00
(52) U.S. Cl. ..... Plt./331
(58) Field of Search ..... Plt./331

*Primary Examiner*—Kent Bell
(74) *Attorney, Agent, or Firm*—Webb Ziesenheim Logsdon Orkin & Hanson, P.C.

(57) ABSTRACT

A new and distinct early flowering geranium plant with showy pink colored flowers with a distinctive eye above medium green foliage.

1 Drawing Sheet

BOTANICAL CLASSIFICATION

*Pelargonium×domesticum* (regal pelargonium).

VARIETAL DENOMINATION

'Elegance Pink Chiffon'.

BACKGROUND OF THE INVENTION

The present invention comprises a new and distinct cultivar of *Pelargonium×domesticum* known by the varietal name 'Elegance Pink Chiffon'. The new variety was discovered in a selected breeding program in Lompoc, Calif. as Breeder No. 7DG4548-41. The new variety is a result of cross breeding of an unnamed, unpatented seedling (Breeder No. White 1994-6, female) and 'Erin' (male, U.S. Plant Pat. No. 10,021). The new variety exhibits similar plant type to both parents and flower color is intermediate to both parents. The new variety was first asexually reproduced by cuttings in Connellsville, Pa. The new variety has been trial and field tested at Connellsville and has been found to retain its distinctive characteristics and remain true to type through successive propagations.

The cultivar, when grown in a glass greenhouse in Connellsville, Pa. using natural light and temperatures of 60° F. night and 68° F. day, has a response time of 12 weeks from a rooted cutting to flowering in a 6 inch pot. The response time was determined on plants grown in soilless media employing constant fertilizer 150–200 parts per million of nitrogen and potassium in full light.

DESCRIPTION OF THE DRAWING

The accompanying photographic drawing illustrates the new variety, with the color being as nearly true as is possible with color illustrations of this type.

DESCRIPTION OF THE PLANT

The following detailed description sets forth the characteristics of the new cultivar. The data which defines these characteristics were collected by asexual reproductions carried out by Oglevee, Ltd. in Connellsville, Pa. Plants described were about 20 weeks from an unrooted cutting. The color readings were taken on a plant under 65–85 foot candles of fluorescent cool white light. Color references are primarily to The R.H.S. Colour Chart of The Royal Horticultural Society of London.

PLANT

Form: Medium mound; free basal branching.
Height: 28–32 cm from media surface to top of foliage in a 6 inch pot.
Diameter: 25–30 cm.
Strength: Does not require artificial support.
Rooting time: Roots visible to outside of artificial dirt plug in 14–21 days.
Leaves:
*Arrangement.*—Alternate.
*Stipules.*—Two per node.
*Size.*—Length: 5.5–7 cm. Width: 7.5–8.5 cm.
*Shape.*—Reniform; truncate base.
*Apex.*—Slightly pointed.
*Margin.*—Serrately lobed.
*Texture.*—Leathery with slight pubescence.
*Color.*—Upper surface: 137A. Lower surface: 137C.
*Ribs and veins.*—Venation: Palmate. Color: 144C.
Petioles:
*Color.*—144A.
*Length.*—2–3 cm.
Stem:
*Color.*—144A.
*Internode length.*—1–2.5 cm.

THE BUD

Shape when no color showing:
*Overall.*—Elliptical cluster.
*Individual bud.*—Elliptical or oval.
Size when no color showing:
*Overall.*—1.8–2.3 cm across cluster.
*Individual bud.*—1.8–2.5 cm long; 5–8 mm wide.
Number of buds per cluster: 3–5.
Color: 56A.

INFLORESCENCE

Blooming habit: Continuous flowering, large flowers forming full flower heads, early blooming.
Size of umbel: 9–11 cm in diameter.
Borne: Umbel, flowers on pedicel, pedicel on peduncle, 3–5 cm above foliage.

Flowers:

*Form.*—Cupped.

*Number of flowers per umbel.*—3–5.

*Size.*—Diameter: 7–8 cm. Depth: 2.5–4 cm.

Petals

Color: These light colored, showy petals have an eye and venation present on the upper 1–2 petals. The upper petals have a darker cast of pink to them in comparison to the lower 3–4 petals.

*Upper surface.*—With eye: 55C begins on the outer edges and fades to 55D and finally to white 155C. In the middle of the petal, there is a presence of an eye of 59C on the outer edges that progresses to 59A. Venation begins near the eye at 59C and moves to the base fading to 77C. Without eye: 62D begins at the outer edges and fades to 56D and then to white 155C. No venation is present in the lower petals.

*Lower surface.*—Upper 1–2 petals (with eye on front): The edges begin at 56C and fade to white 155C near the base of petal. Venation shows through from the front. Lower 3–4 petals (without eye on front): The edges begin with 69D and slowly fade to white 155C near the base.

*Shape.*—Inverted teardrop to heart shaped.

*Size.*—5–6 cm long; 4.5–5.5 cm wide.

*Apex.*—Rounded.

*Base.*—Pointed.

*Margin.*—Entire.

*Number per flower.*—4–6.

*Texture and appearance.*—Velvety, smooth, highly reflective.

Tonality from a distance: Delicate pink flowers, splashed with a striking eye, that are amassed in a bouquet from atop of a mound of medium green foliage. Older flowers fade to white and create a wonderful multicolor bunch.

Petaloids: Absent.

Pedicel:

*Length.*—2–2.3 cm.

*Color.*—144A.

Peduncle:

*Length.*—4—5 cm.

*Color.*—144A.

Lasting quality: Umbels last 14–21 days.

Disease/pest resistance: No unusual susceptibility to diseases or pests has been noted to date.

REPRODUCTIVE ORGANS

Stamens:

*Anthers.*—3–4 mm.

*Filaments.*—Length: 1.5–2.2 cm. Color: Pale pink. Pollen: Golden orange.

Pistils:

*Number.*—One.

*Length.*—2.2–2.4 cm.

*Stigma.*—Number: One. Color: Deep purple.

*Style.*—Length: 1.1–1.3 cm. Color: Purple-red.

*Ovaries.*—Superior, pubescent, 8–9 mm long, 2–3 mm wide, green.

Fruit: None observed.

I claim:

1. A new and distinct variety of geranium plant substantially as shown and described.

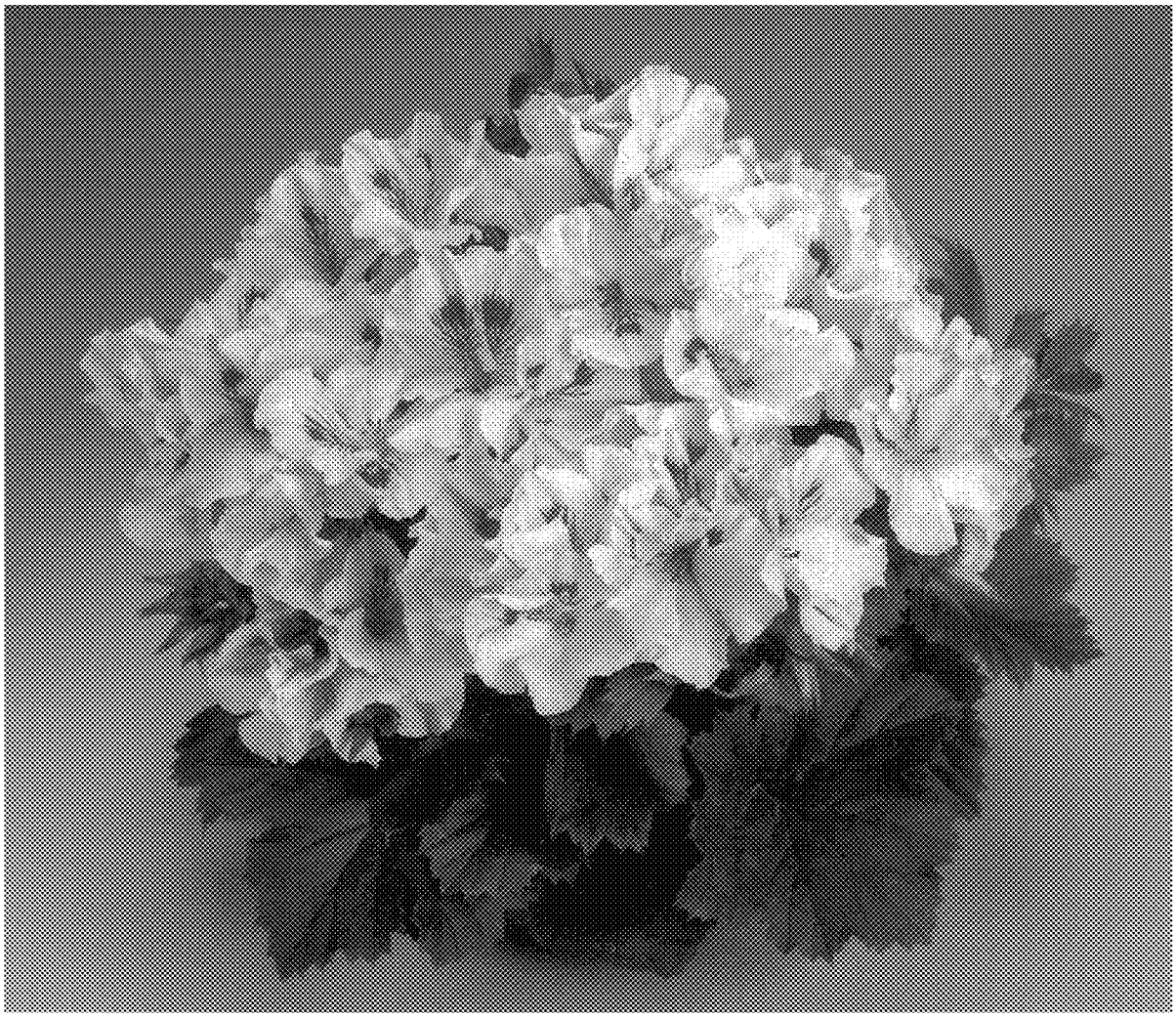

* * * * *